United States Patent [19]

Jaeggi

[11] Patent Number: 5,281,748
[45] Date of Patent: Jan. 25, 1994

[54] N-SUBSTITUTED AMINOMETHANEDIPHOSPHONIC ACIDS

[75] Inventor: Knut A. Jaeggi, Basel, Switzerland

[73] Assignee: Ciba-Geigy Corp., New York, N.Y.

[21] Appl. No.: 936,982

[22] Filed: Aug. 21, 1992

[30] Foreign Application Priority Data

Aug. 27, 1991 [EP] European Pat. Off. ........ 91810682.4

[51] Int. Cl.$^5$ .......................... C07F 9/38; A61K 31/66
[52] U.S. Cl. ........................................ 562/13; 558/158
[58] Field of Search ......................... 562/13; 558/158; 514/102, 107

[56] References Cited

U.S. PATENT DOCUMENTS

| | | | |
|---|---|---|---|
| 3,919,297 | 11/1975 | Krueger et al. | 562/13 |
| 4,761,406 | 8/1988 | Flora et al. | 514/86 |
| 4,927,814 | 5/1990 | Gall et al. | 514/108 |
| 4,942,157 | 7/1990 | Gall et al. | 514/108 |
| 5,036,058 | 7/1991 | Jaeggi | 514/86 |

FOREIGN PATENT DOCUMENTS

| | | |
|---|---|---|
| 0464509 | 1/1992 | European Pat. Off. ............. 562/13 |
| 0491374 | 6/1992 | European Pat. Off. . |

OTHER PUBLICATIONS

Minne et al., The Hypercalcaemic Syndrome in Rats Bearing the Walker Carcinosarcoma 256. Acta Endocrinologica, 78, pp. 613–624 (1975).
Kaibara et al., Pathogenetic Difference between Collagen Arthritis and Adjuvant Arthritis. J. Exp. Med. 159, pp. 1388–1396 (1984).
Newbould, Chemotherapy of Arthritis induced in Rats by Mycobacterial Adjuvant, Brit. J. Pharmacol., 21, pp. 127–136 (1963).
Patent Abstr. Japan, vol. 3, No. 63 (C–47) May 30, 1979 of JP 54–37829 (1979).
Chem Abst 89, 221805f (1978).
Chem Abst 85, 33126d (1976).
Derwent Abst. 83-766213 of EP 88359 (1983).
Derwent Abstr. 46125w (1975).
Derwent Abstr. 17167x (1976).
Derwent Abstr. 87-079621 (1987).
Derwent Abstr. 88-029414 (1988).

*Primary Examiner*—JoséG. Dees
*Assistant Examiner*—B. Frazier
*Attorney, Agent, or Firm*—Irving M. Fishman; Karen G. Kaiser; Barbara J. Ikeler

[57] ABSTRACT

N-substituted aminomethanediphosphonic acids of the formula I,

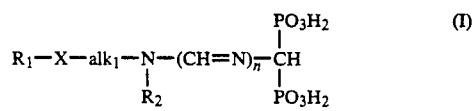

wherein $R_1$, X, $alk_1$, $R_2$ and n are as defined in the description, and salts thereof, have valuable pharmaceutical properties and are effective e.g. in the treatment of conditions which can be associated with disorders of the calcium metabolism. They are manufactured in a manner known per se.

13 Claims, No Drawings

N-SUBSTITUTED AMINOMETHANEDIPHOSPHONIC ACIDS

The invention relates to N-substituted aminomethanediphosphonic acids of the formula I

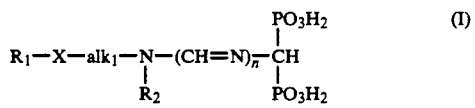

wherein $R_1$ is an aromatic radical, X is oxy, thio, sulphinyl, sulphonyl or a covalent bond, $alk_1$ denotes a divalent aliphatic radical, $R_2$ is hydrogen or a monovalent aliphatic radical, n is 1, or, in case that X is oxy, thio, sulphinyl or sulphonyl, n may also be 0, and to salts thereof, to a process for the preparation of the compounds according to the invention, to pharmaceutical formulations containing the latter and to their use as active compounds for medicaments.

The aromatic radical is, for example, a monocyclic or bicyclic aryl radical, such as a phenyl, naphthyl or indanyl radical.

The aryl radicals mentioned can be substituted, such as monosubstituted, disubstituted or trisubstituted, particularly monosubstituted or disubstituted, especially by lower alkyl, lower alkoxy, lower alkylenedioxy, hydroxyl, trifluoromethyl and/or halogen.

Examples of monovalent aliphatic radicals are lower alkyl or lower alkenyl radicals, while examples of divalent aliphatic radicals are lower alkylene radicals.

Oxy is —O—, thio is —S—, sulphinyl is —SO— and sulphonyl is —SO$_2$—.

In the preceding and following text lower radicals and compounds are to be understood as meaning, for example, radicals and compounds containing up to and including 7, preferably up to and including 4, carbon atoms.

Lower alkyl is, for example, $C_1$–$C_7$alkyl, preferably $C_1$–$C_4$alkyl, such as methyl, ethyl, propyl, isobutyl or butyl, but can also be e.g. isobutyl, secondary butyl, tertiary butyl or a pentyl, hexyl or heptyl group. In particular, lower alkyl is methyl.

Lower alkenyl is, for example, $C_2$–$C_4$alkenyl, such as vinyl, allyl or but-2-enyl, but can also be a $C_5$–$C_7$alkenyl group, such as pentyl, hexenyl or heptenyl.

Lower alkylene is, for example, $C_2$–$C_6$alkylene, such as 1,2-ethylene, 1,3-propylene, 1,4-butylene or 1,5-pentylene.

Lower alkoxy is, for example, $C_1$–$C_7$alkoxy, preferably $C_1$–$C_4$alkoxy, such as methoxy, ethoxy, propyloxy, isopropyloxy or butyloxy, but can also be e.g. isobutyloxy, secondary butyloxy, tertiary butyloxy or a pentyloxy, hexyloxy or heptyloxy group.

Lower alkylenedioxy is, for example, methylenedioxy or ethylenedioxy.

Halogen is, for example, bromine, preferably chlorine or fluorine, but may be also iodine.

Examples of salts of compounds of the formula I are salts thereof with pharmaceutically acceptable bases, such as non-toxic metal salts derived from metals of groups Ia, Ib, IIa and IIb, for example alkali metal salts, in particular sodium or potassium salts, alkaline earth metal salts, in particular calcium or magnesium salts, copper, aluminium or zinc salts, and also ammonium salts containing ammonia or organic amines or quaternary ammonium bases, such as aliphatic amines which can be C-hydroxylated, in particular mono-, di- or tri-lower alkylamines, for example methylamine, ethylamine or diethylamine, mono-, di- or tri-(hydroxy-lower alkyl)-amines, such as ethanolamine, diethanolamine or triethanolamine, tris-(hydroxymethyl)-methylamine or 2-hydroxy-tertiary butylamine, or N-(hydroxy-lower alkyl)-N,N-di-lower alkylamines or N-(polyhydroxy-lower alkyl)-N-lower alkylamines, such as 2-(dimethylamino)-ethanol or D-glucamine, or quarternary aliphatic ammonium hydroxides, for example tetrabutylammonium hydroxide. Both complete and partial salts, i.e. salts containing 1, 2, 3 or 4, preferably 2, equivalents of base per mole of acid of the formula I are embraced.

The compounds of the formula I and their salts have valuable pharmacological properties. In particular they have a pronounced regulating action on the calcium metabolism of warm-blooded animals. Thus in rats they effect a pronounced inhibition of bone resorption which can be demonstrated both in the test set-up specified in Acta Endocrinol. 78, 613–24 (1975) and by means of the PTH-induced increase in the serum calcium level after subcutaneous administration in doses of about 0.01 to about 1.0 mg/kg, and in the TPTX-(thyroparathyroidectomised) rat model by means of the experimental hypercalcaemia initiated by vitamin $D_3$ after the administration of doses of about 0.003 to about 0.05 mg/kg subcutaneously and, in part, also perorally. The tumour hypercalcaemia induced by Walker-256 tumours is also inhibited after peroral administration of about 1.0 to about 100 mg/kg. They also exhibit, in doses of about 0.01 to about 1.0 mg/kg subcutaneously a marked inhibition of the progress of chronic arthritic processes in adjuvant arthritis of rats in the test-set up of Newbold, Brit. J. Pharmacology 21, 127 (1963) and of Kaibara et al., J. Exp. Med. 159, 1388–96 (1984). The indications of tumour-induced hypercalcaemia, bone metastases and Paget's disease are prominent in this respect.

The compounds of the formula I and salts thereof are therefore excellently suitable for use as active compounds for medicaments for the treatment of diseases which can be associated with disturbances of calcium metabolism, for example inflammatory processes in joints, degenerative processes in articular cartilage, osteoporosis, periodontitis, hyperparathyroidism and calcium deposits in blood vessels or in prosthetic implants.

The invention relates primarily to compounds of the formula I wherein $R_1$ is a phenyl or naphthyl radical which radical is unsubstituted or mono-, di- or tri-substituted by substituents selected from lower alkyl, lower alkoxy, lower alkylenedioxy, hydroxyl, halogen and trifluoromethyl, X is oxy, thio, sulphinyl, sulphonyl or a covalent bond, $alk_1$ is lower alkylene, $R_2$ is hydrogen, lower alkyl or lower alkenyl, n is 1, or, in case that X is oxy, thio, sulphinyl or sulphonyl, n may also be 0, and salts thereof, in particular pharmaceutically acceptable salts thereof.

In particular, the invention relates to compounds of the formula I wherein $R_1$ is a phenyl radical which is unsubstituted or mono- or disubstituted by substituents selected from $C_1$–$C_4$alkyl, $C_1$–$C_4$alkoxy, $C_1$–$C_4$alkylenedioxy, hydroxyl, halogen and trifluoromethyl, X is oxy, thio, sulphonyl or a covalent bond, $alk_1$ is $C_2$–$C_6$alkylene, $R_2$ is hydrogen or $C_1$–$C_4$alkyl, n is 1, or, in case that X is oxy, thio or sulphonyl, n may also be 0, and to salts thereof, in particular pharmaceutically acceptable salts thereof.

The invention relates especially to compounds of the formula I wherein $R_1$ is phenyl which is unsubstituted or substituted by $C_1$-$C_4$alkyl, $C_1$-$C_4$alkoxy, hydroxyl, halogen or trifluoromethyl, X is oxy, thio or a covalent bond, $alk_1$ is $C_2$-$C_4$alkylene, $R_2$ is hydrogen or $C_1$-$C_4$alkyl, n is 1, or, in case that X is oxy or thio, n may also be 0, and to salts thereof, in particular to pharmaceutically acceptable salts thereof.

First and foremost, the invention relates to compounds of the formula I wherein $R_1$ is phenyl which is unsubstituted or substituted by $C_1$-$C_4$alkyl, $C_1$-$C_4$alkoxy, hydroxyl or halogen, X is oxy or thio, $alk_1$ is $C_2$-$C_4$alkylene, $R_2$ is hydrogen or $C_1$-$C_3$alkyl, and n represents 1, and to salts thereof, in particular to pharmaceutically acceptable salts thereof.

The invention relates especially to the compounds of the formula I mentioned in the examples and to salts thereof, in particular pharmaceutically acceptable salts thereof.

The compounds of formula I can be prepared in a manner known per se, for example by a) in a compound of the formula II

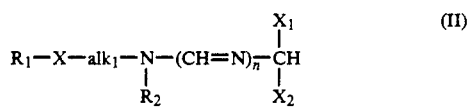

in which $R_1$, n, X, $alk_1$, $R_2$ and $alk_2$ are as defined above, $X_1$ is a functionally modified phosphono group and $X_2$ is a free or functionally modified phosphono group, converting functionally modified phosphono $X_1$ and, if appropriate, $X_2$ into the free phosphono group, or b) for the manufacture of a compound of formula I having n=1, reacting a compound of formula III

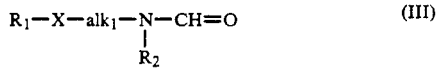

wherein $R_1$, X, $alk_1$ and $R_2$ are as defined under formula I, or a functional derivative thereof, with a compound of formula IV,

or a suitable salt thereof; or c) for the manufacture of a compound of formula I having n=0, reacting a compound of formula IIIa

wherein $R_1$, X and $alk_1$ are as defined under formula I and $Y_3$ is reactive esterified hydroxyl, with a compound of formula IVa

wherein $R_2$ is as defined under formula I, or a suitable salt thereof; and, if desired, converting a resulting compound into another compound of the formula I, separating a mixture of isomers obtainable in accordance with the process into the components and isolating the particular preferred isomer and/or converting a free compound obtainable in accordance with the process into a salt or converting a salt obtainable in accordance with the process into the corresponding free compound.

The reactions according to the process and the preparation of novel starting materials or intermediates are effected analogously to the mode of reaction and formation of known starting materials and/or intermediates. The assistants customary in a particular case, such as catalysts, condensation agents and solvolysis agents and/or solvents or diluents and reaction conditions, such as temperature and pressure, and also, if appropriate, protective gases, are used in this regard, even if not mentioned expressly below.

Functionally modified phosphono groups to be converted into phosphono according to process variant a) are present, for example, in an ester form, in particular a diester form of the formula—$P(=O)(OR)_2$ (IIa), in which OR is etherified hydroxyl, in particular lower alkoxy, lower alkanoyloxy-lower alkoxy or a phenoxy or α-phenyl-lower alkoxy group which is unsubstituted or substituted by lower alkyl, lower alkoxy, halogen, trifluoromethyl and/or hydroxyl, or is silyloxy, such as tri-lower alkylsilyloxy.

The conversion of functionally modified phosphono groups into free phosphono groups is effected in a customary manner, such as by hydrolysis, for example in the presence of a mineral acid, such as hydrochloric or sulphuric acid, at about 80° C. to about 110° C., for example at the boil, or, preferably, by reaction with a tri-lower alkyl halogenosilane, for example trimethylchlorosilane or especially trimethyliodosilane or trimethylbromosilane, preferably in methylene chloride within the temperature range from about 0° C. to about 40° C., followed by treatment with water. When a compound of the formula II is reacted with a tri-lower alkyl halogenosilane, silylated intermediates of hitherto not exactly known structure are formed which which, when triturated with water or with aqueous alcohols, are converted into the diphosphonic acids of formula I.

Compounds of the formula II which serve as starting materials for process variant a) can, for example, be prepared by condensing compounds of the formulae V and VI,

in which one of the groups $Y_1$ and $Y_2$ denotes a reactive esterified hydroxy group, such as halogen, especially chloro, bromo or iodo, or, in the case of $Y_1$, a sulphonyloxy group, for example, a lower alkansulphonyloxy, especially methanesulphonyloxy, an optionally substituted benzenesulphonyloxy group, especially benezene-, p-bromobenzene- or p-toluenesulphonyloxy, or a sulphonyloxy group of the formula $R_1$—X—$alk_1$—O—$SO_2$—O—$alk_1$—X—$R_1$, and the other one represents a group of the formula —$N(R_2)$—H (VII); or $Y_1$ denotes a group of the formula —$N(R_2)$—CH=O (VIII), wherein the formyl group is preferably functionally modified, such as acetalised, for example, with a lower alkanol or a lower alkanediol, and $Y_2$ is amino.

Compounds of the formula V, wherein $Y_1$ is reactive esterified hydroxy or a group (VII), and compounds of the formula VI, wherein $Y_2$ is halogen, amino or a group (VII) are known in the art. Compounds of the formula V, wherein $Y_1$ represents a group —N(R$_2$)—CH=O (VIII) can be manufactured, for example, by reacting a corresponding compound of the formula $R_1$—X—alk$_1$—NH$_2$ (IX) with a N,N-disubstituted formamide, such as N,N-dimethyl formamide, or, preferably an acetal thereof, such as a N,N-dimethyl formamide di-lower alkyl or lower alkylene acetal, especially N,N-dimethyl formamide dimethyl acetal.

Process (b): Preferably, a functional derivative of a compound of formula III is used.

A functional derivative of a compound of formula III is preferably a di-lower alkyl acetal, especially dimethyl acetal.

Optionally, the reaction is carried out in the presence of a condensating agent, e.g. POCl$_3$.

Process (c): Reactive esterified hydroxyl $Y_3$ is defined in the same manner as Y, $Y_1$ and $Y_2$ above and represents e.g. halogen.

The conversion according to process (c) represents a well-known N-alkylation reaction via nucleophilic substitution.

Processes (b) and (c) are similar to the manufacture of the compounds of formula II as described under process (a).

Compounds obtainable in accordance with the process can be converted in a customary manner into other compounds of the formula I.

Thus a monovalent aliphatic radical $R_2$ can be introduced into compounds of the formula I in which $R_2$ is hydrogen in a customary manner by reaction with a reactive ester of the formula $R_2$—Y (X) in which Y is reactive esterified hydroxyl, for example a halogen atom, such as chlorine, bromine or iodine, or a sulphonyloxy group, for example methanesulphonyloxy or p-toluenesulphonyloxy, or by reaction with an aliphatic aldehyde or ketone of the formula $R_2$=O (Xa) under reducing conditions. The reaction with oxo compounds (Xa) is carried out, for example, in the presence of a reducing agent, for example, of an alkali metal borohydride, for example sodium cyanoborohydride, by catalytic hydrogenation or by treatment with formic acid. In a preferred embodiment a corresponding compound of the formula Ia can be substituted by a lower alkyl radical $R_2$ under reducing conditions by means of a lower alkanal, for example formaldehyde, and formic acid.

It is also possible to oxidize compounds of the formula I in which X is thio in a customary manner to give the corresponding compound of the formula I in which X is sulphinyl or sulphonyl, for example by treatment with an inorganic peroxy compound, for example hydrogen peroxide, persulphuric acid, or an organic peroxy compound, such as perbenzoic acid or m-chloroperbenzoic acid.

It is also possible to introduce substituents into the radical $R_1$ of compounds of the formula I, for example lower alkyl by reaction with a lower alkyl halide in the presence of aluminium trichloride, lower alkoxy, for example by nitration, reduction of the nitro group to give the amino group, diazotisation of the latter and treatment of the diazonium salt formed with the corresponding lower alkanol under hot conditions, and halogen, for example, by treatment with chlorine or bromine, advantageously in the presence of a Lewis acid, for example iron-III chloride. It is also possible, however, to replace halogen by trifluoromethyl, for example by treatment with trifluoroiodomethane in the presence of copper powder or copper-I iodide.

Depending on the choice of starting materials and procedures, the novel compounds can be present in the form of one of the possible isomers, for example, depending on the number of asymmetric carbon atoms, as optical isomers, such as in the form of an enantiomer, such as antipodes or diastereomers or mixtures thereof, such as mixtures of enantiomers, for example racemates, mixtures of diastereomers or mixtures of racemates.

Resulting mixtures of diastereomers and mixtures of racemates can be separated into the pure diastereomers or racemates, respectively, in a known manner on the basis of the physico-chemical differences between the constituents, for example by chromatography and/or fractional crystallization. Resulting racemates can also be resolved into the optical antipodes by known methods, for example by recrystallisation from an optically active solvent, with the help of microorganisms by reacting a compound of the formula I with an optically active base or with an optically active alcohol and separating the resulting diastereomeric esters, for example on the basis of their different solubilities, into the diastereomers, from which the enantiomers can be liberated by the action of suitable agents. Racemates of the formula I can also be resolved, by reaction with an optically active base, into mixtures of the diastereomeric salts and separation of the latter into the diastereomers, from which the enantimers can be liberated in the manner customary in each case.

Examples of optically active bases which are customary for this purpose are optically active alkaloids, such as quinine, cinchonine, brucine and the like, or, in particular, α-phenylethylamine.

It is also possible to convert resulting salt-forming compounds into salts in a manner known per se, for example by reacting a solution of the free solvent in a suitable solvent or solvent mixture with an appropriate base or with a suitable ion exchanger.

Resulting salts can be converted into the free compounds in a manner known per se, for example by treatment with an acid, such as a mineral acid, for example hydrochloric acid.

Resulting salts can be converted into other salts in a manner known per se, for example by treatment with a suitable base, such as sodium hydroxide or potassium hydroxide, ammonia or a suitable amine.

The compounds of the formula I, including their salts, can also be obtained in the form of hydrates or can occlude the solvent used for crystallization.

Because of the close relationship between the novel compounds in the free form and in the form of their salts, what is stated in the preceding and following text in respect of the free compounds or the salts thereof also applies by analogy to the corresponding salts and free compounds, respectively.

The invention also relates to those embodiments of the process in which a compound obtainable as an intermediate at any stage of the process is used as the starting material and the remaining stages are carried out, or a starting material is used in the form of a salt, or, in particular, is formed under the conditions of the reaction.

The novel starting materials, which have been specially developed for the preparation of the compounds according to the invention, in particular the choice of starting materials leading to the compounds of the formula I which have been characterized initially as preferred, the processes for their preparation and their use as intermediates also form an object of the invention.

The novel compounds of the formula I can, for example, be used in the form of pharmaceutical formulations containing a therapeutically effective amount of the active substance, if appropriate together with inorganic or organic, solid or liquid, pharmaceutically acceptable excipients which are suitable e.g. for enteral, such as oral, parenteral or transdermal administration. Thus tablets or gelatin capsules containing the active ingredient together with diluents, for example lactose, dextrose, sucrose, mannitol, sorbitol or cellulose, and/or lubricants, for example silica, talc, stearic acid or salts thereof, such as magnesium stearate or calcium stearate, and/or polyethylene glycol. Tablets can also contain binders, for example magnesium aluminium silicate, starches, such as maize, wheat, rice or arrow root starch, gelatin, tragacanth, methyl cellulose, sodium carboxymethyl cellulose and/or polyvinylpyrrolidone, and, if desired, disintegrants, for example starches, agar, alginic acid or a salt thereof, for example sodium alginate, and/or effervescent mixtures, or absorbents, dyes, flavouring substances and sweeteners. The novel compounds of the formula I can also be used in the form of formulations capable of being administered parenterally or in the form of infusion solutions. Such solutions are preferably isotonic aqueous solutions or suspensions, it being possible to prepare the latter before use, for example in the case of lyophilised formulations containing the active ingredient on its own or together with an excipient, for example mannitol. The pharmaceutical formulations can be sterilized and/or contain adjuncts, for example preservatives, stabilizers, wetting agents and/or emulsifiers, solubilisers, salts for regulating the osmotic pressure and/or buffers. The present pharmaceutical formulations, which, if desired can contain further pharmacologically active substances, are prepared in a manner known per se, for example by means of conventional mixing, granulating, coating, solution or lyophilising processes, and contain from about 0.1% to 100%, in particular from about 1% to about 50% of the active ingredient, up to about 100% in the case of lyophilisates.

Products suitable for parenteral administration are primarily aqueous solutions of the active ingredient in a water-soluble form, for example in the form of a water-soluble, pharmaceutically acceptable salt, and also suspensions of the active ingredient, such as oily injection suspensions, in which case suitable lipophilic solvents or vehicles, such as fatty oils, for example sesame oil, or synthetic fatty esters, for example ethyl oleate, and also triglycerides are used, or aqueous injection suspensions containing substances which increase the viscosity, for example sodium carboxymethyl cellulose, sorbitol and/or dextran, and, if appropriate stabilizers.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The invention also relates to the use of compounds of the formula I for the treatment of diseases due to disturbances of calcium metabolism, preferably by the provision of pharmaceutical formulations. The dosage of the compound of the formula I according to the invention can depend on various factors such as the mode of application, species, age and/or individual condition. Single doses contain, for example, from about 0.01 to about 0.1 mg, preferably 0.02 to 0.08 mg, per kilogram of body weight in the case of parenteral administration and about 0.2 to about 2.5 mg, preferably 0.3 to 1.5 mg, per kilogram of body weight in the case of oral administration. The preferred single doses thus amount to about 0.5 to 5.0 mg in the case of parenteral administration and to about 10 to 100 mg in the case of oral administration. The doses to be administered daily in the case of oral administration are between about 0.25 and about 10 mg/kg and for warm-blooded animals having a body weight of about 70 kg, preferably between about 20 and about 500 mg.

The following examples serve to illustrate the invention; temperatures are quoted in degrees Centigrade and pressures in mbar.

EXAMPLE 1

3.5 g (0.0073 mol) of N-(3-phenoxypropyl)-N-methyl-formamidinomethanediphosphonic acid tetraethyl ester are dissolved in 30 ml of dichloromethane, and 4.7 ml (0.036 mol) of trimethylbromosilane are added. After 72 hours at room temperature, the solvent is removed under reduced pressure. The remaining oil is dissolved in warm 95% aqueous methanol. On cooling, N-(3-phenoxypropyl)-N-methylformamidinomethanediphosphonic acid of m.p. 211°–212° (decomp.) is obtained.

The starting material may be obtained as follows:

16.5 g (0.1 mol) of N-(3-phenoxypropyl)-N-methylamine and 15.0 ml (0.1 mol) of N,N-dimethylformamide dimethyl acetal are stirred at 120° for 18 hours. After distillation under reduced pressure, N-(3-phenyoxypropyl)-N-methyl-formamide dimethyl acetal of b.p. 64°–67° (0.001 mbar) is obtained.

2.43 g (0.008 mol) of aminomethylenediphosphonic acid tetraethyl ester and 1.91 g (0.008 mol) of N-(3-phenoxypropyl)-N-methyl-formamide dimethyl acetal are dissolved in 30 ml of tetrahydrofuran and stirred under reflux for 5 hours. After removal of the solvent under reduced pressure, raw N-(3-phenoxypropyl)-N-methyl-formamidinomethanediphosphonic acid tetraethyl ester is obtained which may be used without further purification.

EXAMPLE 2

4.0 g (0.008 mol) of N-(2-phenylthioethyl)-N-methyl-formamidinomethanediphosphonic acid tetraethyl ester are dissolved in 30 ml of dichloromethane, and 5.2 ml (0.040 mol) of trimethylbromosilane are added. After 72 hours at room temperature, the solvent is removed under reduced pressure. The remaining oil is dissolved in warm 95% aqueous methanol. On cooling, N-(2-phenylthioethyl)-N-methyl-formamidinomethanediphosphonic acid of m.p. 215°–216° (decomp.) is obtained.

The starting material may be obtained as follows:

8.0 g (0.048 mol) of N-(2-phenylthioethyl)-N-methylamine and 7.0 ml (0.048 mol) of N,N-dimethylformamide dimethyl acetal are stirred at 120° for 18 hours. After distillation under reduced pressure, N-(2-phenylthioethyl)-N-methyl-formamide dimethyl acetal of b.p. 85°–89° (0.001 mbar) is obtained.

2.43 g (0.008 mol) of aminomethylenediphosphonic acid tetraethyl ester and 1.93 g (0.008 mol) of N-(2-phenylthioethyl)-N-methyl-formamide dimethyl acetal are dissolved in 30 ml of tetrahydrofuran and stirred under reflux for 5 hours. After removal of the solvent under reduced pressure, raw N-(2-phenylthioethyl)-N-methyl-formamidinomethanediphosphonic acid tetraethyl ester is obtained which may be used without further purification.

Example 3

2.9 g (0.0065 mol) of N-(2-phenylethyl)-N-methyl-formamidinomethanediphosphonic acid tetraethyl ester are dissolved in 30 ml of dichloromethane, and 4.2 ml (0.0325 mol) of trimethylbromosilane are added. After 72 hours at room temperature, the solvent is removed under reduced pressure. The remaining oil is dissolved in warm 95% aqueous methanol. On cooling, N-(2-phenylethyl)-N-methyl-formamidinomethanediphosphonic acid of m.p. 223°–224° (decomp.) is obtained.

The starting material may be obtained as follows:

6.76 g (0.050 mol) N-(2-phenylethyl)-N-methyl-amine and 7.4 ml (0.050 mol) N,N-dimethylformamide dimethyl acetal are stirred under reflux in a bath of 120° for 18 hours. After distillation under reduced pressure, N-(2-phenylethyl)-N-methyl-formamide dimethyl acetal of b.p. 52°–54° (0.001 mbar) is obtained.

3.03 g (0.01 mol) of aminomethylenediphosphonic acid tetraethyl ester and 2.1 g (0.01 mol) of N-(2-phenylethyl)-N-methyl-formamide dimethyl acetal are dissolved in 30 ml of tetrahydrofuran and stirred under reflux for 5 hours. After removal of the solvent under reduced pressure, raw N-(2-phenylethyl)-N-methyl-formamidinomethanediphosphonic acid tetraethyl ester is obtained which may be used without further purification.

EXAMPLE 4

3.0 g (0.0068 mol) of N-(3-phenoxypropyl)aminomethanediphosphonic acid tetraethyl ester are dissolved in 20 ml of dichloromethane, and 4.4 ml (0.0343 mol) of trimethylbromosilane are added. After 72 hours at room temperature, the solvent is removed under reduced pressure. The remaining oil is dissolved in warm 95% aqueous methanol. On cooling, N-(3-phenoxypropyl)aminomethanediphosphonic acid of m.p. 226°–228° (decomp.) is obtained.

The starting material may be obtained as follows:

3.03 g (0.01 mol) of aminomethylenediphosphonic acid tetraethyl ester, 2.3 g (0.01 mol) of 3-phenoxypropylbromide and 1.4 g (0.01 mol) of potassium carbonate are dissolved in 50 ml of dioxane and stirred under reflux for 24 hours. The major part of the solvent is distilled off, and the residue is partitioned between water and ethyl acetate. The organic layer is separated, washed with water, dried over sodium sulphate and evaporated to dryness yielding raw N-(3-phenoxypropyl)aminomethanediphosphonic acid tetraethyl ester which may be used without further purification.

EXAMPLE 5

In an analogous manner as described in Examples 1 to 4, also the following compounds can be manufactured:

(a) N-[3-(4-chlorophenoxy)propyl]-N-methyl-formamidinomethanediphosphonic acid, m.p. 204°–205° C.;

(b) N-[3-(4-methylphenoxy)propyl]-N-methyl-formamidinomethanediphosphonic acid; and (c) N-[3-(4-methoxyphenoxy)propyl]-N-methyl-formamidinomethanediphosphonic acid.

EXAMPLE 6

4.7 g (0.0084 mol) of N-[3-(4-chlorophenoxy)propyl]-N-methyl-formamidinomethanediphosphonic acid tetraethyl ester are dissolved in 30 ml of dichloromethane, and 5.5 ml (0.042 mol) of trimethylbromosilane are added. After 72 hours at room temperature, the solvent is removed under reduced pressure. The remaining oil is dissolved in warm 95% aqueous methanol. On cooling, N-[3-(4-chlorophenoxy)propyl]-N-methyl-formamidinomethanediphosphonic acid of m.p. 204°–205° C. (decomposition) is obtained.

The starting material is prepared as follows:

4.0 g (0.02 mol) of N-[3-(4-chlorophenoxy)propyl]-N-methyl-amine and 3.0 ml (0.02 mol) of N,N-dimethylformamide dimethyl acetal are stirred at 120° C. for 18 hours. After distillation under reduced pressure, N-[3-(4-chlorophenoxy)propyl]-N-methyl-formamide dimethyl acetal of b.p. 92° C. (0.005 mbar) is obtained.

2.54 g (0.0084 mol) of aminomethylenediphosphonic acid tetraethyl ester and 2.30 g (0.0084 mol) of N-[3-(4-chlorophenoxy)propyl]-N-methyl-formamide dimethyl acetal are dissolved in 30 ml of tetrahydrofuran and stirred under reflux for 5 hours. After removal of the solvent under reduced pressure, raw N-[3-(4-chlorophenoxy)propyl]-N-methylformamidinomethanediphosphonic acid tetraethyl ester is obtained which may be used without further purification.

EXAMPLE 7

Tablets each containing 50 mg of N-(3-phenoxypropyl)-N-methyl-formamidinomethanediphosphonic acid or a salt thereof, for example the disodium salt, can be prepared as follows:

| Composition (10,000 tablets) | |
|---|---|
| Active ingredient | 500.0 g |
| Lactose | 500.0 g |
| Potato starch | 325.0 g |
| Gelatin | 8.0 g |
| Talc | 60.0 g |
| Magnesium stearate | 10.0 g |
| Silicon dioxide (finely divided) | 20.0 g |
| Ethanol | q.s. |

The active ingredient is mixed with the lactose and 292 g of potato starch, and the mixture is moistened with an ethanolic solution of the gelatin and granulated through a sieve. After the granules have dried, the remainder of the potato starch, the magnesium stearate and the silicon dioxide are admixed and the mixture compressed to give tablets each weighing 145.0 mg and containing 50.0 mg of active ingredient, which can, if desired, be provided with breaking grooves to enable the dosage to be more finely adjusted.

EXAMPLE 8

Lacquered tablets each containing 100 mg of N-(3-phenoxypropyl)-N-methyl-formamidinomethanediphosphonic acid or a salt thereof, for example the disodium salt, can be prepared as follows:

| Composition (for 1,000 lacquered tablets) | |
|---|---|
| Active ingredient | 100.0 g |
| Lactose | 100.0 g |
| Maize starch | 70.0 g |
| Talc | 8.5 g |
| Calcium stearate | 1.5 g |
| Hydroxypropylose | 2.36 g |
| Shellac | 0.64 g |
| Water | q.s. |
| Methylene chloride | q.s. |

The active ingredient, the lactose and 40 g of the maize starch are mixed, moistened with a paste prepared (by heating) from 15 g of maize starch and water and granulated. The granules are dried and the remainder of the maize starch, the talc and the calcium stearate are added and mixed with the granules. The mixture is compressed to give tablets (weight: 280 mg), and these tablets are lacquered with a solution of the hydroxypropylmethyl cellulose and the shellac in methylene chloride; final weight of the lacquered tablet: 283 mg.

EXAMPLE 9

Hard gelatin capsules each containing 100 mg of active ingredient, for example N-(3-phenoxypropyl)-N-methyl-formamidinomethanediphosphonic acid or a salt thereof, for example the disodium salt, can, for example, be prepared in the following way:

| Composition (for 1,000 capsules) | |
|---|---|
| Active ingredient | 100.0 g |
| Microcrystalline cellulose | 30.0 g |
| Sodium laurylsulphate | 2.0 g |
| Magnesium stearate | 8.0 g |

Using a sieve of mesh width 0.2 mm, the sodium laurylsulphate is sieved onto the lyophilised active ingredient. The two components are intimately mixed. The microcrystalline cellulose is then sieved onto the mixture through a sieve of mesh width 0.9 mm. The mixture is again intimately mixed for 10 minutes. Finally, the magnesium stearate is sieved on using a sieve of mesh width 0.8 mm. After being mixed for a further 3 minutes, 390 mg of the resulting formulation are filled into each hard gelatin capsule of size 0.

EXAMPLE 10

A 0.2% injection or infusion solution of N-(3-phenoxypropyl)-N-methyl-formamidinomethanediphosphonic acid or one of its salts, for example its disodium salt, can, for example, be prepared in the following way:

| Composition (for 1,000 ampoules) | |
|---|---|
| Active ingredient | 5.0 g |
| Sodium chloride | 22.5 g |
| Phosphate buffer pH 7.4 | 300.0 g |
| De-ionised water | ad 2500.0 ml |

The active ingredient is dissolved in 1000 ml of water and the solution is filtered through a microfilter. The buffer solution is added and the mixture is made up to 2500 ml with water. Dosage unit forms are prepared by filling 1.0 to 2.5 ml in each case into glass or plastic ampoules, which then contain 2.0 or 5.0 mg, respectively, of active ingredient in each case.

EXAMPLE 11

Pharmaceutical formulations containing another compound of the formula I according to one of Examples 2 to 6 can also be prepared in a manner analogous to that in Examples 7 to 10.

I claim:

1. An N-substituted aminomethanediphosphonic acid of the formula I

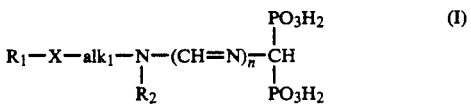

in which $R_1$ is an aromatic radical, X is oxy, thio, sulphinyl, sulphonyl or a covalent bond, $alk_1$ denotes a divalent aliphatic radical, $R_2$ is hydrogen or a monovalent aliphatic radical, n is 1, or a salt thereof.

2. A compound of the formula

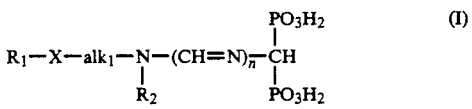

wherein $R_1$ is a phenyl or naphthyl radical which radical is unsubstituted or mono-, di- or tri-substituted by substituents selected from lower alkyl, lower alkoxy, lower alkylenedioxy, hydroxyl, halogen and trifluoromethyl, X is oxy, thio, sulphinyl, sulphonyl or a covalent bond, $alk_1$ is lower alkylene, $R_2$ is hydrogen, lower alkyl or lower alkenyl, n is 1, or a salt thereof.

3. A compound as claimed in claim 1 of the formula I wherein $R_1$ is a phenyl radical which is unsubstituted or mono- or disubstituted by substituents selected from $C_1$–$C_4$alkyl, $C_1$–$C_4$alkoxy, $C_1$–$C_4$alkylenedioxy, hydroxyl, halogen and trifluoromethyl, X is oxy, thio, sulphonyl or a covalent bond, $alk_1$ is $C_2$–$C_6$alkylene, $R_2$ is hydrogen or $C_1$–$C_4$alkyl, n is 1, or a salt thereof.

4. A compound as claimed in claim 1 of the formula I wherein $R_1$ is phenyl which is unsubstituted or substituted by $C_1$–$C_4$alkyl, $C_1$–$C_4$alkoxy, hydroxyl, halogen or trifluoromethyl, X is oxy, thio or a covalent bond, $alk_1$ is $C_2$–$C_4$alkylene, $R_2$ is hydrogen or $C_1$–$C_4$alkyl, n is 1, or a salt therof.

5. A compound as claimed in claim 1 of the formula I wherein $R_1$ is phenyl which is unsubstituted or substituted by $C_1$–$C_4$alkyl, $C_1$–$C_4$alkoxy, hydroxyl or halogen, X is oxy or thio, $alk_1$ is $C_2$–$C_4$alkylene, $R_2$ is hydrogen or $C_1$–$C_3$alkyl, and n represents 1, or a salt thereof.

6. N-(3-phenoxypropyl)-N-methyl-formamidinomethanediphosphonic acid according to claim 2 or a pharmaceutically acceptable salt thereof.

7. N-(2-phenylthioethyl)-N-methyl-formamidinomethanediphosphonic acid according to claim 2 or a pharmaceutically acceptable salt thereof.

8. N-(2-phenylethyl)-N-methyl-formamidinomethanediphosphonic acid according to claim 2 or a pharmaceutically acceptable salt thereof.

9. N-[3-(4-chlorophenoxy)propyl]-N-methyl-formamidinomethanediphosphonic acid according to claim 2 or a pharmaceutically acceptable salt thereof.

10. A pharmaceutical composition comprising a compound according to claim 1 and at least one pharmaceutically acceptable carrier.

11. A method of treating conditions which can be associated with disorders of the calcium metabolism in mammals which comprises administering to a mammal in need thereof a therapeutically effective amount of a compound of formula I according to claim 1, or a pharmaceutically acceptable salt thereof.

12. A pharmaceutical composition comprising a compound according to claim 2 and at least one pharmaceutically acceptable carrier.

13. A method of treating conditions which are associated with disorders of the calcium metabolism in mammals which comprises administering to a mammal in need thereof a therapeutically effective amount of a compound according to claim 2, or a pharmaceutically acceptable salt thereof.

* * * * *